(12) United States Patent
Hasegawa (10) Patent No.: US 7,699,811 B2
(45) Date of Patent: Apr. 20, 2010

(54) PRE-FILLED SYRINGE

(75) Inventor: Mitsuru Hasegawa, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/652,001

(22) Filed: Jan. 11, 2007

(65) Prior Publication Data

US 2007/0161961 A1   Jul. 12, 2007

(30) Foreign Application Priority Data

Jan. 12, 2006   (JP)  ............................. 2006-005430

(51) Int. Cl.
*A61M 5/00* (2006.01)
(52) U.S. Cl. ..................... 604/191; 604/85; 604/89; 604/122; 604/187; 604/218
(58) Field of Classification Search ............. 604/82–85, 604/89–92, 122, 187, 191, 218, 222, 124, 604/125
See application file for complete search history.

(56) References Cited

U.S. PATENT DOCUMENTS

| 4,235,235 A | 11/1980 | Bekkering | 128/218 P |
| 4,573,972 A | 3/1986 | Kamstra | 604/191 |
| 4,668,223 A | 5/1987 | Grotenhuis | 604/191 |
| 4,792,329 A * | 12/1988 | Schreuder | 604/90 |
| 6,544,233 B1 * | 4/2003 | Fukui et al. | 604/191 |
| 2002/0045865 A1 * | 4/2002 | Mitomi et al. | 604/207 |
| 2004/0097875 A1 | 5/2004 | Bae | 604/89 |

FOREIGN PATENT DOCUMENTS

| EP | 1 013 299 A1 | 6/2000 |
| EP | 1 190 727 A2 | 3/2002 |
| EP | 1 192 966 A1 | 4/2002 |
| EP | 1 728 528 A1 | 12/2006 |
| JP | 62-58745 B2 | 12/1987 |
| JP | 4-46152 B2 | 7/1992 |
| JP | 9-225032 A1 | 9/1997 |
| JP | 2002-177391 A1 | 6/2002 |
| WO | 2005/089837 * | 9/2005 |
| WO | 2005/089837 A1 | 9/2005 |

* cited by examiner

*Primary Examiner*—Kevin C Sirmons
*Assistant Examiner*—Bhisma Mehta
(74) *Attorney, Agent, or Firm*—Kubovcik & Kubovcik (57) ABSTRACT

A pre-filled syringe including a barrel 1, a base end gasket 4 which is fluid-tightly slidable in the barrel 1, a front end gasket 8 which is fluid-tightly slidable in the barrel 1, and a nozzle part 2 provided in a front end of the barrel 1, wherein the nozzle part 2 includes a front end gasket accommodation part 23 which is capable of accommodating the front end gasket 8, and liquid flow passages 21 extending in an axial direction in an inner periphery wall, through which a liquid medicine can pass when the front end gasket 23 is accommodated in the front end gasket accommodation part 23, and a sectional area of a front end of the liquid flow passages 21 is smaller than a sectional area of a base end.

12 Claims, 5 Drawing Sheets

PRE-FILLED SYRINGE

TECHNICAL FIELD

The present invention relates to a pre-filled syringe. More specifically, it relates to a pre-filled syringe in which an inside of a barrel is partitioned by a gasket, a liquid medicine or a solution and a powder medicine are stored, and which includes a nozzle part to which an injection needle is detachably attached.

RELATED ART

A conventional preparation of liquid medicine is such that ampules, vials, or the like in which medicines are separately stored until just before use, are opened by using a throwaway syringe or injection needle, or the like and medicines are prepared at the time of use, and then the prepared medicine is used. However, this method is intricate in its operation, so that a lot of time and effort is required, and in addition, there is a fear that bacteria in the air will invade the medicine, and a high possibility that foreign objects like such as particles of glass in the ampule, particles of rubber in the vial, and the like are mixed in the medicine (i.e., coring). For solving these problems, a pre-filled syringe as a combined syringe and container, for providing stability when a medicine and a liquid medicine are stored, is marketed, and has been adopted in many clinics and hospitals because it is excellent in its convenience.

As a conventional pre-filled syringe, a device as disclosed in JP-B-62-58745 is enumerated. In JP-B-62-58745, as shown in FIG. 1 thereof, stoppers are fluid-tightly and slidably inserted into a front end and a base end of a tubular body whose both ends are open, and a liquid medicine is filled between the stoppers and can be safely kept. And, a needle holder to which an injection needle has been attached is fluid-tightly fitted to the front end of the tubular body, and a finger grip is fitted to a roar end of the tubular body. An inside of the needle holder in a base end side has an inner diameter which is somewhat larger than an outer diameter of the front end stopper, and has a front end stopper accommodation part having an axial length which is somewhat longer than a length of the front end stopper. In an inner wall of the needle holder, there is or are provided one or plural groove hole or holes communicating from the base end to an inner bore of the injection needle of the front end, and, if the base end stopper is moved forward by a plunger rod connected to the base end stopper by being inserted from the rear end of the tubular body, a liquid medicine kept in the tubular body between the front end and base end stoppers moves forward, and thus a seal is released by the fact that the front end stopper enters the front end stopper accommodation part, so that the liquid medicine in the tubular body flows to the inner bore of the injection needle while passing through the groove hole or holes to thereby be capable of performing an injection.

In the above pre-filled syringe, before the plunger rod is pushed, since the liquid medicine kept in the tubular body is isolated also from external bacteria, it is safe and, if the injection needle is attached beforehand, convenience is good as well, so that it can be said that it is the most suitable one as a structure of a pre-filled syringe.

By the way, in the pre-filled syringe having a structure as described above, although a risk of coring can be solved, when an injection is performed by moving the front end stopper forward from the tubular body to an inside of the front end stopper accommodation part of the needle holder, it is necessary beforehand to expel air bubbles remaining in the liquid medicine having been kept in the tubular body. However, since a rear face of the front end stopper and a front face of the base end stopper are smooth faces perpendicular to an axis of the tubular body, there has existed a problem that, after the front end stopper enters the front end stopper accommodation part, even if the liquid medicine is pushed by additionally moving forward the base end stopper, air bubbles in the tubular body are left in the rear face of the front end stopper and are difficult to expel to the outside. Further, since the front end and base end stoppers are made of a rubber, the air bubbles are liable to adhere to a peripheral face in comparison with glass, a plastic or the like, which forms the tubular body, and, also from this point, there has been a problem that the air bubbles are difficult to expel from the injection needle attached to the needle holder.

As one means of solving this problem, a device as disclosed in JP-B-4-46152 is enumerated. As shown in FIG. 1 in JP-B-4-46152, the device includes a cylindrical ampule whose front end and base end are open, a separation stopper fluid-tightly partitioning an inside of the ampule to a front chamber and a rear chamber, a plunger placed in a base end side relative to the separation stopper and sealing the inside of the ampule, a plunger rod connected to a base end of the plunger, a seal stopper placed in a front end side relative to the separation stopper and sealing the inside of the ampule, a needle holder to which an injection needle is fluid-tightly engaged with the front end of the ampule, and a plunger rod provided in a base end part of the ampule, and a bulge part bulging outwardly in a radial direction is formed between the separation stopper of the ampule and the seal stopper.

The rear chamber is formed in the ampule between the separation stopper and the plunger with a solution kept therein, while the front chamber is formed in the ampule between the separation stopper and the seal stopper with a powder preparation kept therein. An inside of the needle holder in a base end side has an inner diameter which is somewhat larger than an outer diameter of the seal stopper, and has a seal stopper accommodation part having an axial length which is somewhat longer than a length of the seal stopper. In an inner wall of the needle holder, there is or are provided one or plural groove bore or bores communicating from the base end to an inner bore of the injection needle of the front end. If the plunger is moved forward by the plunger rod connected to the seal stopper by being inserted from the rear end of the ampule, a solution kept in the ampule between the separation stopper and the plunger moves forward and, if a rear end of the separation stopper reaches a rear end of the bulge part of the ampule, the solution flows into the front chamber existing in the separation stopper and the seal stopper through the bulge part, thereby dissolving the medicine. Since almost all of the front chamber is filled with air and it is necessary to violently shake the device to dissolve the medicine in some cases, air bubbles adhere to a rear face of the seal stopper and discharge of the air bubbles to the outside is difficult. However, by providing several notches in a peripheral end edge of the seal stopper rear face, discharge of the air bubbles to the outside is made easy (see also, e.g., JP-A-2002-177391).

However, there are problems that since notch provided in the peripheral end edge of the rear face of the seal stopper extends to a side face, airtightness of a seal part is reduced, and that even if the seal stopper is moved forward during preparation for dissolution, since a liquid flow is made through the notch just before the seal stopper is completely accommodated in a seal stopper accommodation part existing in an inside in a base end side of the needle holder, some gap occurs in a forward portion of the seal stopper existing in an inside of the needle holder, so that when the plunger rod is pushed to the end on administering an injection to a patient it does not move smoothly, thereby generating an uncomfortable feeling. Further, there is also a problem that if the medicine and the solution are shaken in order to be dissolved, medicine, which is insufficiently dissolved, enters through the notch into a concave between seals existing in an outer periphery of the seal stopper and clogs the concave, and generally the notch is made small in order to reduce a residual liquid as much as possible, so that the residual liquid is difficult to return to the front chamber. Additionally, there has been a problem that in a case where a distance between the mutual notches is large like a case where an inner capacity of the pre-filled syringe is large and thus its, inner diameter becomes large, unless an operator operates such that a position of the notch is positioned upward, the air bubbles adhere to the rear face of the seal stopper and remain intact, so that there is a tear that the air bubbles are not discharged to the outside and there are changes per one operation.

DISCLOSURE OF THE INVENTION

The present invention is one having been made in view of the above circumstances, and its object is to provide a pre-filled syringe in which, in carrying out an injection by the pre-filled syringe, it becomes possible to easily expel air bubbles in the liquid medicine stored or dissolution-prepared in a container to the outside through the injection needle and, in a two-chamber type pre-filled syringe, it is possible to prevent uneven dissolution of the liquid medicine during shaking from occurring.

Whereupon, the present inventor devised the present invention as a result of earnestly repeating studies in order to solve the above-mentioned problems. That is, the present invention is:

(1) a pre-tilled syringe including a barrel whose front end and base end are open, a base end gasket in a base end side in the barrel and fluid-tightly slidable in the barrel, a front end gasket in a front end side in the barrel and fluid-tightly slidable in the barrel, and a nozzle part provided in the front end of the barrel, characterized in that the nozzle part includes a front end gasket accommodation part which is capable of accommodating the front end gasket, and liquid flow passages extending in an axial direction in an inner periphery wall, through which a liquid medicine can pass when the front end gasket is accommodated in the front end gasket accommodation part, and a sectional area of a front end of the liquid flow passages is smaller than a sectional area of a base end;

(2) a pre-filled syringe according to (1), wherein there are formed an intermediate gasket between the front end gasket in the barrel and the base end gasket which fluid-tightly partitions an inside of the barrel into a front chamber and a rear chamber, and a bypass bulging outwardly in a radial direction between the intermediate gasket of the barrel and the front end gasket;

(3) a pre-filled syringe according to (1) or (2), characterized in that a sectional area of the liquid flow passages becomes gradually smaller from the base end toward the front end;

(4) a pre-filled syringe according to (1)-(3), wherein in an outer periphery edge of a rear end face of the front end gasket, a concave part or concave parts, extending inwardly in a radial direction, is or are formed between the annular ribs of the front end gasket; or (5) a pre-filled syringe according to (2)-(4), wherein the intermediate gasket includes an annular seal part which contacts an inner wall of the barrel and fluid-tightly partitions the syringe into the front chamber and the rear chamber, and a bypass communication passage that is a spiral groove formed in an outer wall of the intermediate gasket, which communicates the front chamber with the rear chamber while cooperating with the bypass.

According to the present invention, in performing an injection it is possible to make it easy to discharge air bubbles in the liquid medicine in the pre-filled syringe to the outside through the injection needle without impairing the convenience in preparing the liquid medicine or a storage property possessed by a conventional pre-filled syringe. Further, even if the inner diameter of the barrel becomes large with an increase in the inner capacity of the pre-filled syringe, it is possible to make it easy to certainly discharge the air bubbles in the liquid medicine in the pre-filled syringe to the outside in spite of the operation. Additionally, in the two-chamber type pre-filled syringe in which the medicine and the liquid medicine are mixed and dissolved, it is possible to provide a pre-filled syringe which is capable of preventing uneven dissolution of the medicine by shaking during preparation from occurring. Further, also a structure of a nozzle member is comparatively simple as to only provide a concave liquid flow passage in an inner wall face, so that there is no unreasonableness in a mold design and it can be easily manufactured.

BEST MODE FOR CARRYING OUT THE INVENTION

Next, an embodiment of the present invention is explained on the basis of the drawings.

Figure 1:
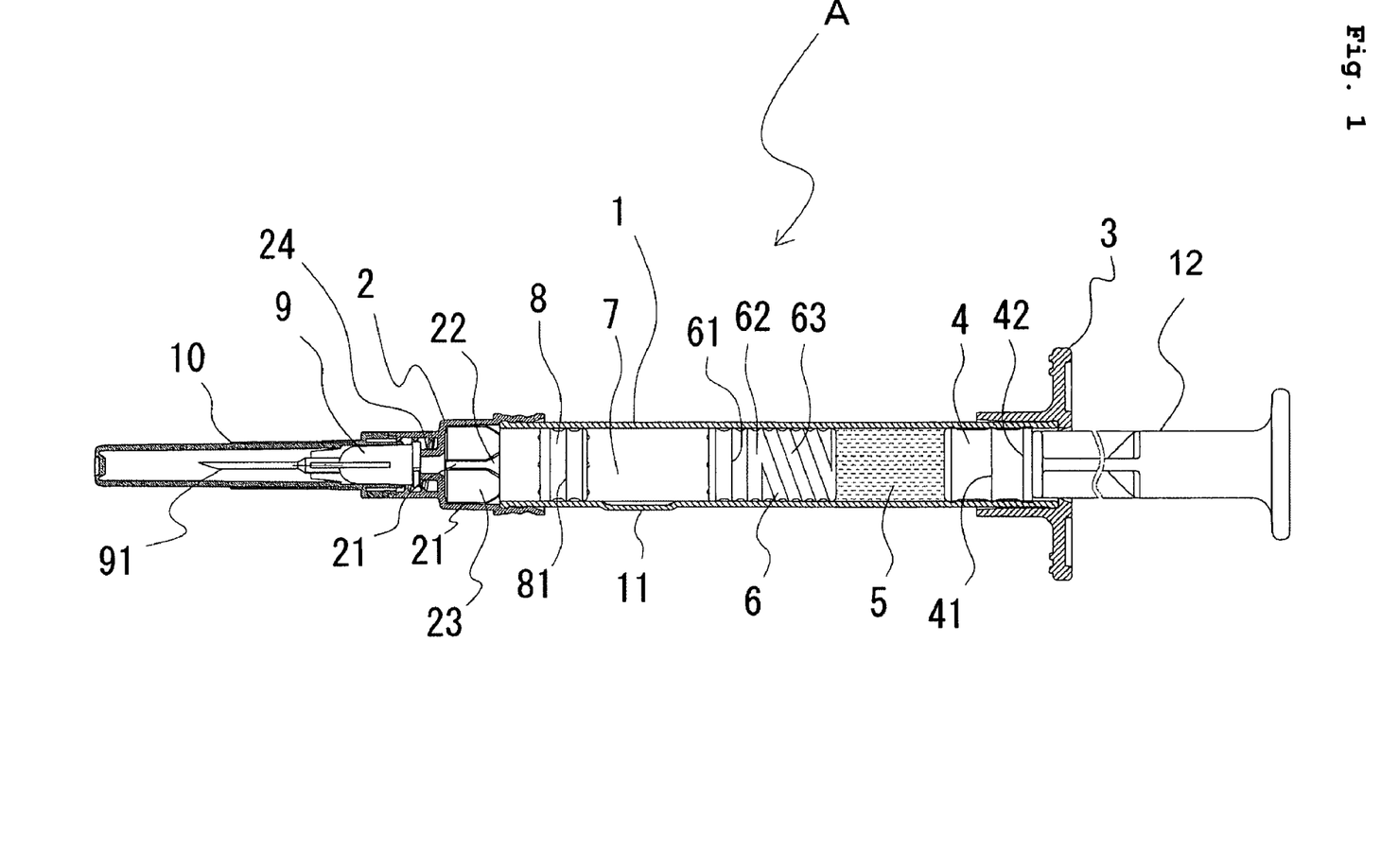
FIG. 1 is a cross-sectional view showing a pre-filled syringe according to a first embodiment of the present invention.
Figure 2:
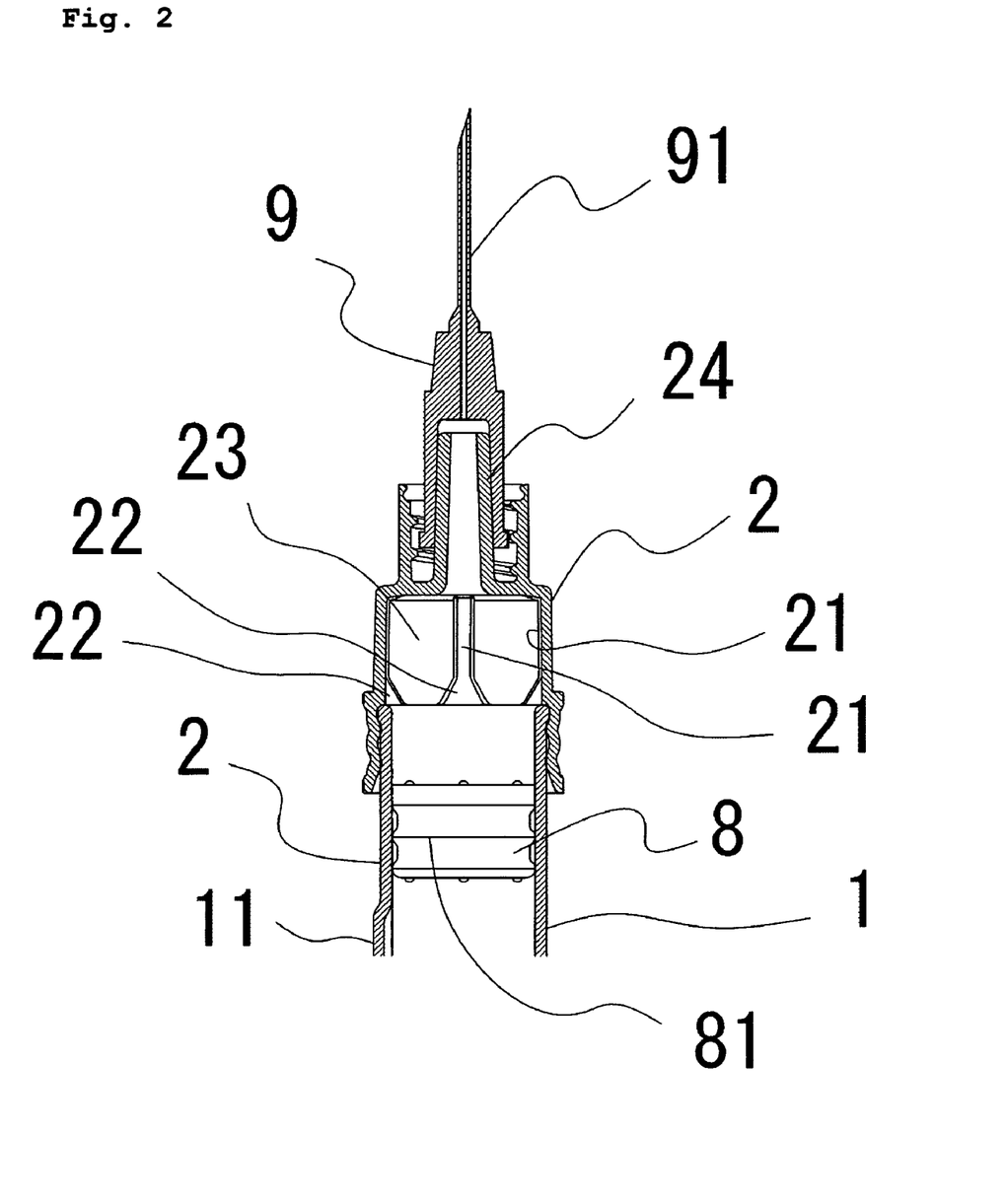
FIG. 2 is a longitudinal sectional view showing the position of a front end gasket before use of the pre-filled syringe according to a first embodiment of the present invention.
Figure 3:
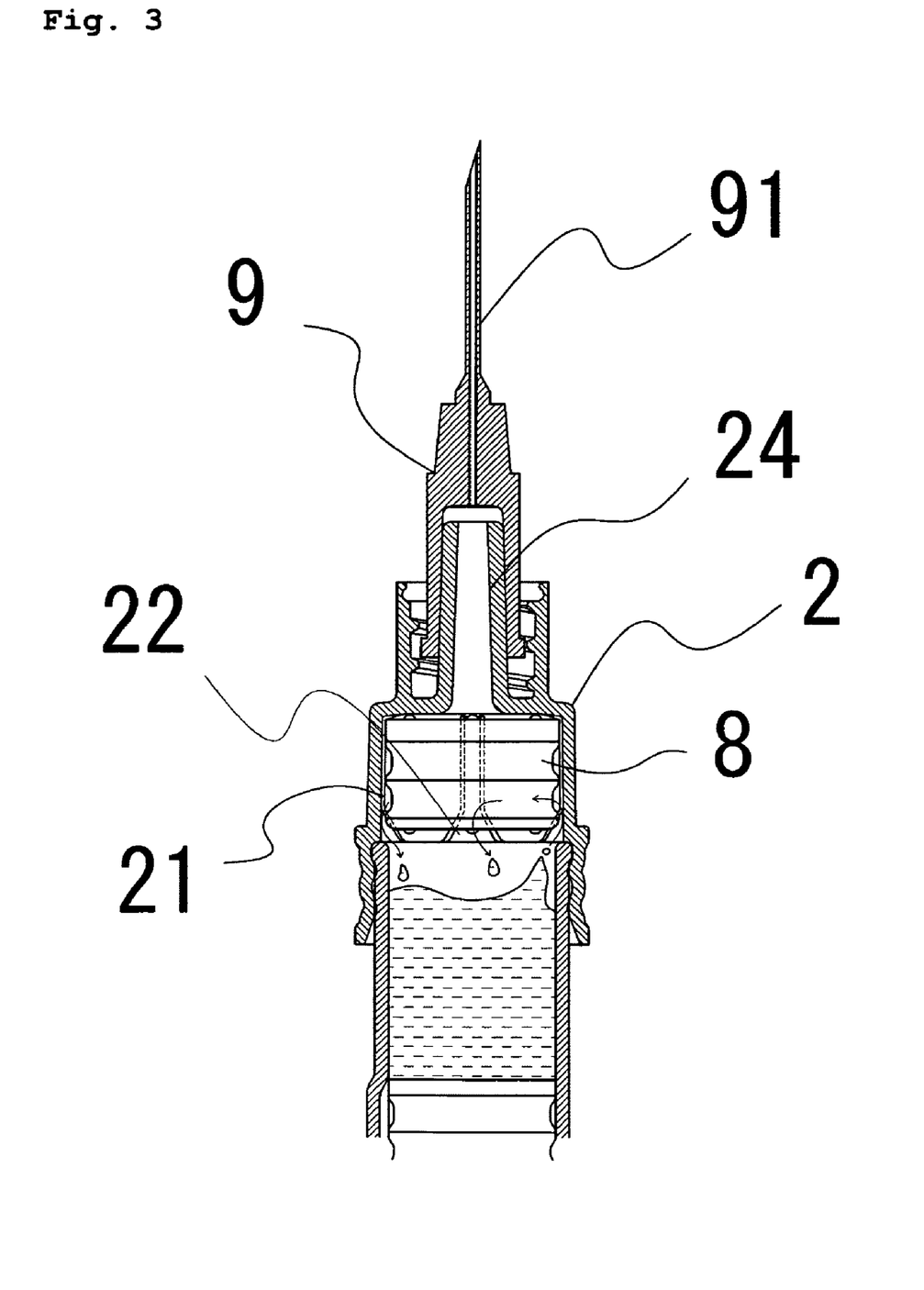
FIG. 3 is a longitudinal sectional view showing a state of being shaken during dissolution preparation and operation positions of the front end and intermediate gaskets of the pre-filled syringe according to a first embodiment of the present invention.
Figure 4:
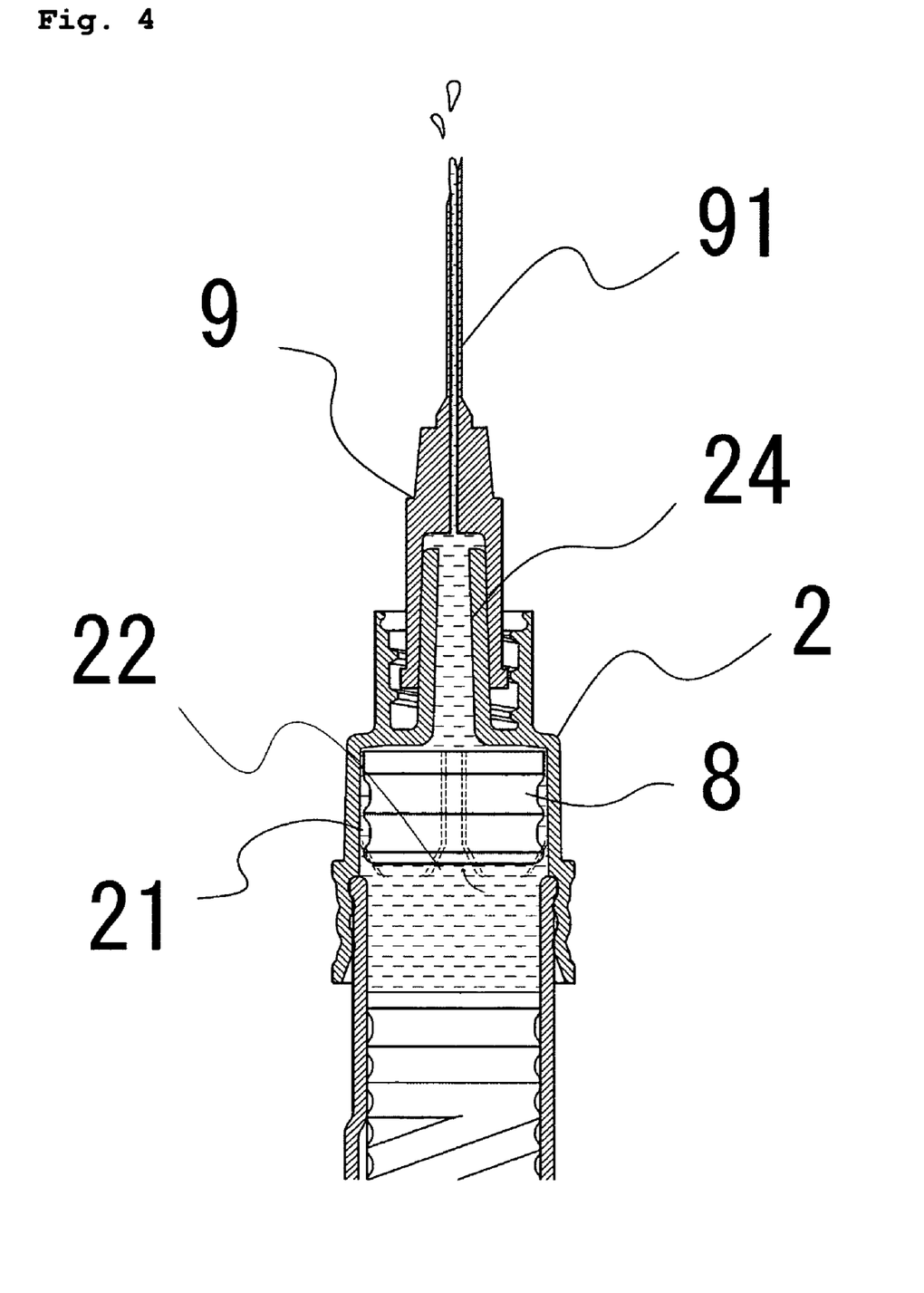
FIG. 4 is a longitudinal sectional view showing a state in which air bubbles in a front chamber are being discharged during preparation for an injection and the operation positions of the front end and intermediate gaskets of the pre-filled syringe according to a first embodiment of the present invention.

FIG. 1-FIG. 4 are views showing a two-chamber type pre-filled syringe that is a first embodiment of the present invention. FIG. 1 is a cross-sectional view of the same, and FIGS. 2-4 are longitudinal sectional views explaining use of the pre-filled syringe of the first embodiment. FIG. 2 is a view showing a state before dissolution is performed and position of the front end gasket, FIG. 3 is a view showing a state in which the pre-filled syringe is being shaken for dissolution and operation positions of the front end and intermediate gaskets, and FIG. 4 is a view showing a state in which air bubbles are being discharged during preparation for injection and operation positions of the front end and intermediate gaskets.

Figure 5:
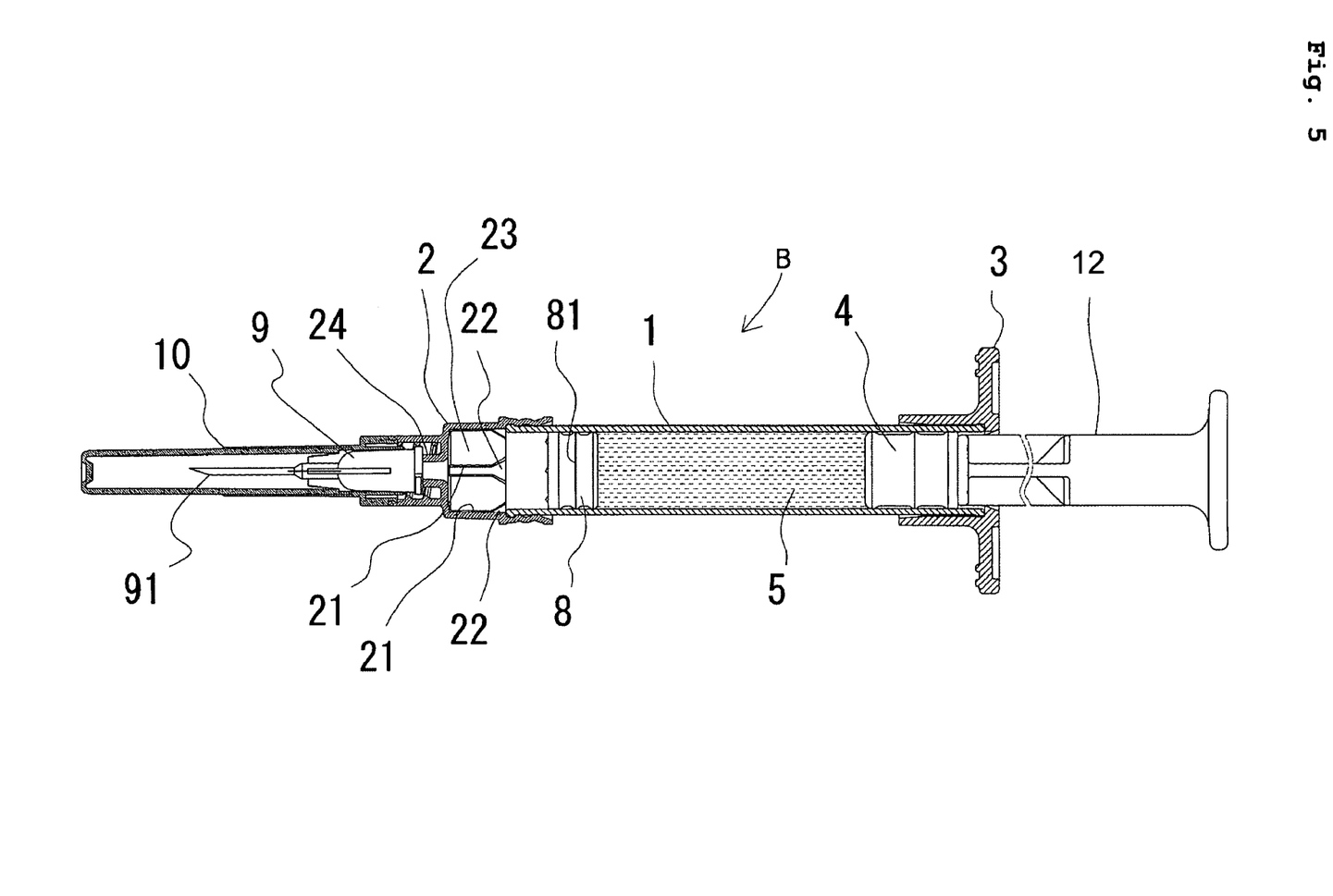
FIG. 5 is a cross-sectional view showing a pre-filled syringe according to another embodiment of the present invention.

FIG. 5 is a cross-sectional view showing a one-chamber type pre-filled syringe that is a second embodiment of the present invention.

Embodiment 1

A pre-filled syringe A that is one implementation mode of the present invention has, among the above characteristics, (1), (2), (3) and (5), and additionally it is desirable to have characteristic (4). Concretely, as shown in FIG. 1-FIG. 4, the pre-filled syringe A is a two-chamber type pre-filled syringe possessing a barrel 1 whose front end and base end are open, an intermediate gasket 6 fluid-tightly partitioning an inside of the barrel 1 into a front chamber and a rear chamber, a base end gasket 4 in a base end side relative to the intermediate gasket 6 and sealing the inside of the barrel 1, a plunger rod 12 connected to a base end of the base end gasket 4, a front end gasket 8 placed in a front end side relative to the intermediate gasket 6 and sealing the inside of the barrel 1, a nozzle member 2 which is fluid-tightly engaged with a front end of the barrel 1 and to which an injection needle 9 is detachably attached, and a flange part 3 provided in a base end part of the barrel 1, wherein a bypass 11 bulging outwardly in a radial direction is formed between the intermediate gasket 6 and the front end gasket 8 of the barrel 1, and the syringe comprises a constitution in which the nozzle member 2 includes a front end gasket accommodation part 23 capable of accommodating the front end gasket 8, at least two liquid flow passages 21 extending in an axial direction in an inner periphery wall, through which the liquid medicine can pass when the front end gasket 8 has been accommodated in the front end gasket accommodation part 23, and a wide width part 22 of the liquid flow passage, in which a sectional area of the front end of the liquid flow passage becomes smaller than a sectional area of the base end.

The nozzle member 2 is a tubular member whose front end has a nozzle 24 capable of discharging a liquid medicine and a base end that is open and to which the barrel 1 can be fluid-tightly fitted. And, in its inside, there is formed the front end gasket accommodation part 23 which is capable of accommodating the front end gasket 8, which is mentioned later. Further, as shown in FIG. 2, in an inner wall of the front end gasket accommodation part 23, there is formed liquid flow passage 21 through which the liquid medicine can pass when the front end gasket 8 has been accommodated in the front end gasket accommodation part 23. This liquid flow passage 21 is a groove having been concavely provided in a side wall and a top face of the front end gasket accommodation part 23, and its one end is connected to an inner cavity of the nozzle 24 and the other end can communicate with the barrel 1. Incidentally, an axial length of the liquid flow passage 21 must be longer than an axial length of the front end gasket 8 and, if it is shorter, it is impossible to discharge the liquid medicine. Further, the liquid flow passage 21 possesses a wide width part 22 in which a width widens in a base end of the side wall such that a sectional area of the front end becomes smaller than that of the base end of the side wall when seen in the sectional area of the front end of the side wall. Further, as shown in FIG. 2, the nozzle 24 can be a male luer to which injection needle 9 can be connected.

As a material for forming the nozzle member 2, although there are enumerated, e.g., polyolefin resins such as polyethylene and polypropylene, polyvinyl chloride, PET (polyethylene terephthalate), EVA (ethylene-vinyl acetate copolymer), EVOH (ethylene-vinyl alcohol copolymer), polyamide, polyvinylidene chloride, polyvinyl fluoride, polytrifluorochloroethylene, polyester, nylon, mixtures thereof and laminated bodies thereof, the material is not limited especially if it is known for use as a medical equipment material and does not interact with the medicine accommodated in the barrel 1, and also there is no fear of elution into the medicine or the like.

Incidentally, it is rather desirable that the injection nozzle 9 is generally attached to the nozzle 24. In this case, as shown in FIG. 1, a needle protector 10 is mounted on the injection needle 9. The material for forming the needle protector 10 is not limited, especially if it is known for use as a medical equipment material and has a rigidity which prevents fear that the injection needle 9 will be bent or damaged by a load from the outside.

In a case where the injection needle 9 is not attached to the nozzle 24, a cap (not shown in the drawing) is used to seal the nozzle 24. As a material for forming the cap, although there can be suitably adopted an elastic material such as, e.g., butyl rubber, silicone rubber, a thermoplastic elastomer and a silicone elastomer, the material is not limited especially if it is known for use as a medical equipment material and can seal the nozzle 24.

The barrel 1 is a tubular member whose front end and base end are open, and the flange part 3 for applying fingers is formed at its base end, and its front end is fluid-tightly mounted to the nozzle member 2. The front end of the barrel 1 is fluid-tightly sealed by the front end gasket 8, and the base end is fluid-tightly sealed by the base end gasket 4. The intermediate gasket 6 is inserted into the barrel 1, and the inside of the barrel 1 is fluid-tightly partitioned into a front chamber 7 and a rear chamber 5 by the intermediate gasket 6. Additionally, in a wall of the front chamber 7, the bypass 11 is formed in the axial direction of the barrel 1 so as to bulge radially outward. As a material for forming the barrel 1, although there are enumerated, e.g., glass, polyolefin resins such as polyethylene and polypropylene, polyvinyl chloride, PET (polyethylene terephthalate), EVA (ethylene-vinyl acetate copolymer), EVOH (ethylene-vinyl alcohol copolymer), polyamide, polyvinylidene chloride, polyvinyl fluoride, polytrifluorochloroethylene, polyester, nylon, mixtures thereof and laminated bodies thereof, the material is not limited especially if it is known for use as a medical equipment material and does not interact with the medicine accommodated in the barrel 1, and also there is no fear of elution into the medicine or the like.

In the rear chamber 5, a solution is accommodated. It is desirable that, as the solution accommodated in the rear chamber 5, there is accommodated a solution like physiological salt solution and glucose solution, or a liquid chemical as a liquid medicine. In the front chamber 7, a powder medicine is accommodated. As the medicine accommodated in the front chamber 7, although a powder medicine which is unstable if dissolved with the liquid chemical in the rear chamber 5, e.g., lyophilized preparation of an antibiotic or the like, is desirable, a form of the medicine accommodated in the front chamber 7 is not especially limited, and it may be a liquid-like medicine which is necessary to be mixed just before use.

The front end gasket 8, the base end gasket 4 and the intermediate gasket 6 are all columnar members consisting of an elastic body and have several annular ribs 41, 61, 81 formed in their side faces in a circumferential direction for fluid-tightly contacting with the inner wall of the barrel 1, and are slidable in the barrel 1. Further, as shown in FIG. 1, the ribs of the intermediate gasket 6 may include an annular rib 61 formed in the front end side in the circumferential direction for fluid-tightly contacting the inner wall of the barrel 1, a circumferential groove 62 concavely provided in the circumferential direction while adjoining a base end side of the annular rib 61, and a bypass communication passage 63 with a spiral groove formed in an outer wall of the intermediate gasket 6 communicating the circumferential groove 62 with the rear chanter 5. In this arrangement, since it is possible to avoid distortion of a gasket when the gasket is inserted into the barrel and to shorten an effective seal length which is a distance between annular ribs 61 from a most front end to a most base end by suitably lengthening the length of the gasket, it is possible to shorten a moving distance of the intermediate gasket 6, which is necessary for the rear chanter 5 and the front chanter 7 to communicate through the bypass 11. In addition, an inner pressure of the front chamber 7 is raised by an advance of the intermediate gasket 6 in preparation for dissolution and thus the inside of the front chamber 7 becomes like a compressed air spring and, when the solution flows into the front chamber 7 through the bypass 11, the front end gasket 8 vigorously moves forward and enters the front end gasket accommodation part 23, so that there is an advantage that the liquid medicine is prevented from flying out by its vigorous power from a needle tip 91 of the injection needle 9.

Further, by suitably setting lengths of the annular rib 61, the circumferential groove 62, the communication passage 63 and the base end gasket 4, since it is possible to avoid a fear that, when the liquid medicine in the pre-filled syringe has been wholly discharged, an annular rib 42 existing in a most base end of the base end gasket 4 moves forward beyond a base end of the bypass 11, it is possible to prevent the liquid medicine from leaking to the outside from a base end side of the barrel 1 in a case of a liquid medicine whose toxicity is strong, or the like. As a material for forming the base end gasket 4, although there can be suitably adopted an elastic material such as, e.g., butyl rubber, silicone rubber, a thermoplastic elastomer and a silicone elastomer, the material is not limited especially if it is known for use as a medical equipment material, and generates no interaction with the medicine accommodated in the barrel 1.

A plunger rod 12 is connected to the base end of the base end gasket 4. The plunger rod 12 may be previously connected, or may be connected at a time of use. As a connection method, there are enumerated a friction fit, a mesh and the like. As a material for forming the plunger rod 12, although there may be enumerated a synthetic resin and the like, the material is not especially limited.

Subsequently, there is explained a method of using the pre-filled syringe A of the first embodiment (FIG. 1). When performing an injection with the pre-filled syringe A of the first embodiment, first the pre-filled syringe A is placed in a state that the injection needle 91 is directed upward. If the plunger rod 12 is pushed and moved forward in a front end direction while supporting the flange part 3 by the fingers, the inner pressure of the rear chamber 5 is raised and, accompanying it, the intermediate gasket 6 is also moved forward. In a point in time at which the annular rib 61 of the intermediate gasket 6 has moved beyond a base end of the bypass 11, the solution in the rear chamber 5 flows to the front chamber 7 while passing through the communication passage 63 and the circumferential groove 62. Accompanying this, since the inner pressure in the front chamber 7 is raised, the front end gasket 8 moves forward and enters into the front end gasket accommodation part 23 of the nozzle member 2, and thus the seal provided by the front end gasket 8 is released, a front end face of the base end gasket 4 butts against a base end face of the intermediate gasket 6, i.e., a gas in the front chamber 7 is discharged from the needle tip 91 of the injection needle to the outside until the gas existing in the front chamber 7 and a whole quantity of the solution in the rear chamber 5 are moved.

Next, the pre-filled syringe is shaken with an amount of force complying with a dispersion property of the powder medicine, thereby dissolving the powder medicine in the liquid chemical and making the liquid medicine. In a base end of the front end gasket accommodation part 23, since the liquid flow passage is widened at 22, a liquid surface is wavy, or undulates, during shaking time and, even if the liquid medicine enters between an inner periphery wall of the front end gasket accommodation part 23 and a side face of the front end gasket 8 when dissolution is insufficient, it immediately returns into the front chamber 7.

If the plunger rod 12 is additionally, slowly pushed and advanced in a front end direction while the pre-filled syringe A is kept in the same state, air bubbles of a slight quantity in the liquid medicine, which gather to the base end face of the front end gasket 8 in the barrel 1 and are floating, are liable to be trapped and do not remain at the liquid flow area because a cross-sectional area of the liquid flow passage in the side wall of the front end gasket accommodation part 23 is made smaller in its front end than in its base end and the bubbles are discharged to the outside before the liquid medicine is discharged because flow velocity is increased toward the front end in the liquid flow passage.

Next, the needle protector 10 is removed and the needle tip 91 of the injection needle is pierced into an object portion of a patient, and the plunger rod 12 is slowly pushed, thereby injecting the liquid medicine. From this state, if the plunger rod 12 is additionally strongly pushed, the front end, the intermediate and the base end gaskets 4, 6 and 8 are elastically deformed respectively, so that it is possible to inject the liquid medicine in the pre-filled syringe A without leaving the medicine in the syringe.

A pre-filled syringe B that is another embodiment of the present invention has, among the above characteristics, (2) and (3), and additionally it is desirable to have (4). Concretely, as shown in FIG. 5, the pre-filled syringe B is a one-chamber type pre-filled syringe including a barrel 1 whose front end and base end are open, a base end gasket 4 fluid-tightly and slidably attached to a base end in the barrel 1, a plunger rod 12 connected to the base end of a base end gasket 4, a front end gasket 8 fluid-tightly and slidably attached to the front end in the barrel 1, a nozzle member 2 which is fluid-tightly engaged with the front end of the barrel 1 and to which the injection needle 9 is detachably attached, and a flange part 3 provided at the base end part of the barrel 1. Pre-filled syringe B comprises a construction in which the nozzle member 2 includes the front end gasket accommodation part 23 capable of accommodating the front end gasket 8, at least two liquid flow passages 21 extending in the axial direction in the inner periphery wall, through which the liquid medicine can pass when the front end gasket 8 is accommodated in the front end gasket accommodation part 23, and a wide width part 22 of the liquid flow passage, in which the sectional area in the front end of the liquid flow passage becomes smaller than the sectional area of the base end.

The nozzle member 2 is a tubular member whose front end has a nozzle 24 capable of discharging a liquid medicine and base end which is opened and to which the barrel 1 can be fluid-tightly fitted. And, in its inside, there is formed the front end gasket accommodation part 23 which is capable of accommodating the front end gasket 8, which is mentioned later. Further, as shown in FIG. 5, in the inner wall of the front end gasket accommodation part 23, there is formed the liquid flow passage 21 through which the liquid medicine can pass when the front end gasket 8 has been accommodated in the front end gasket accommodation part 23. This liquid flow passage 21 is a groove concavely provided in the side wall and the top face of the front end gasket accommodation part 23, and its one end is linked to the inner cavity of the nozzle 24 and the other end can communicate with the barrel 1. Incidentally, the axial length of the liquid flow passage 21 must be longer than the axial length of the front end gasket 8. If it is shorter, it is impossible to discharge the liquid medicine. Further, the liquid flow passage 21 possesses wide width part 22 in which the width widens in the base end of the side wall such that a sectional area of the front end becomes smaller than that of the base end of the side wall when seen in a sectional area of the front end of the side wall. Further, as shown in FIG. 2, the nozzle 24 can be in the form of a male luer to which the injection needle 9 can be connected.

As the material for forming the nozzle member 2, although there can be enumerated, e.g., polyolefin resins such as polyethylene and polypropylene, polyvinyl chloride, PET (polyethylene terephthalate), EVA (ethylene-vinyl acetate copolymer), EVOH (ethylene-vinyl alcohol copolymer), polyamide, polyvinylidene chloride, polyvinyl fluoride, polytrifluorochloroethylene, polyester, nylon, mixtures thereof and laminated bodies thereof, the material is not limited especially if it is known for use as a medical equipment material and does not interact with the medicine accommodated in the barrel 1, and also if there is no fear of elution of the material into the medicine or the like. Incidentally, the nozzle member 2 can also be a nozzle part which is formed as one body with the barrel 1.

Incidentally, it is desirable that the injection nozzle 9 is generally attached to the nozzle 24. In this case, as shown in FIG. 1, the needle protector 10 is mounted on the injection needle 9. As the material for forming the needle protector 10, the material is not especially limited if it is known for use as a medical equipment material, and has a rigidity which prevents a fear of the injection needle being bent or damaged by a load from the outside.

In the case where the injection needle 9 is not attached to the nozzle 24, a cap (not shown in the drawing) is used to seal the nozzle 24. As the material for forming the cap, although there can be suitably adopted an elastic material such as, e.g., butyl rubber, silicone rubber, a thermoplastic elastomer and a silicone elastomer, the material is not limited especially if it is known for use as a medical equipment material and can seal the nozzle 24.

The barrel 1 is a tubular member whose front end and base end are open and has flange part 3 for applying fingers formed at its base end and has nozzle member 2 fluid-tightly mounted to its front end. The front end of the barrel 1 is fluid-tightly sealed by the front end gasket 8, and the base end is fluid-tightly sealed by the base end gasket 4, thereby forming a liquid medicine chamber 5. As the material for forming the barrel 1, although there can be enumerated, e.g., glass, polyolefin resins such as polyethylene and polypropylene, polyvinyl chloride, PET (polyethylene terephthalate), EVA (ethylene-vinyl acetate copolymer), EVOH (ethylene-vinyl alcohol copolymer), polyamide, polyvinylidene chloride, polyvinyl fluoride, polytrifluorochloroethylene, polyester, nylon, mixtures thereof and laminated bodies thereof, the material is not limited especially if it is known for use as a medical equipment material and does not interact with the medicine accommodated in the barrel 1, and also if there is no tear of elution of the material into the medicine or the like.

Incidentally, the liquid medicine is accommodated in the liquid medicine chamber 5.

The front end gasket 8 and the base end gasket 4 are all columnar members consisting of an elastic body, have several annular ribs 41, 81 formed in their side faces in the circumferential direction while fluid-tightly contacting the inner wall of the barrel 1, and are slidable in the barrel 1. As the material for forming the gaskets, although there can be suitably adopted an elastic material such as, e.g., butyl rubber, silicone rubber, a thermoplastic elastomer and a silicone elastomer, the raw material thereof is not limited especially if it is known for use as a medical equipment material, and generates no interaction with the medicine accommodated in the barrel 1.

The plunger rod 12 is connected to the base end of the base end gasket 4. The plunger rod 12 may be previously connected, or may be connected at the time of use. As the connection method, there are enumerated a friction fit, the screw connection mesh and the like. As the material for forming the plunger rod 12, although there may be used a synthetic resin and the like, the material is not especially limited.

Subsequently, there is explained a method of using the pre-filled syringe B of the second embodiment (FIG. 5). When injecting using the pre-filled syringe B of the second embodiment, first the pre-filled syringe B is placed in a position in which the injection needle 91 is directed upward. If the plunger rod 12 is then pushed and moved forward in the front end direction while supporting the flange part 3 by the fingers, air bobbles in a slight quantity in the liquid medicine, which gather to the base end face of the front end gasket 8 in the barrel 1 and are floating, are liable to be trapped because the liquid flow passages in the side wall of the front end gasket accommodation part 23 are made smaller in its front end than in its base end when seen in a sectional area, and do not remain and are discharged to the outside ahead of the liquid medicine because the flow velocity is increased.

Next, the needle protector 10 is removed and the needle tip 91 of the injection needle is pierced into an object portion of a patient, and the plunger rod 12 is slowly pushed, thereby injecting the liquid medicine.

From this state, if the plunger rod 12 is additionally, strongly pushed, the front end and the base end gaskets 4 and 8 are elastically deformed respectively, so that it is possible to inject the liquid medicine in the pre-filled syringe B without leaving the liquid medicine in the syringe.

This application claims priority of Japanese patent application No. 2006-005430 filed Jan. 12, 2006, which is incorporated herein by reference.

What is claimed is:

1. A pre-filled syringe comprising a barrel having a front end and base end which are open, a base end gasket which is in a base end side in the barrel and fluid-tightly slidable in the barrel, a front end gasket which is in a front end side in the barrel and fluid-tightly slidable in the barrel, and a nozzle part provided on the front end of the barrel, the nozzle part comprising a front end gasket accommodation part for accommodating the front end gasket; and two or more liquid flow passages with the base end of one liquid flow passage being separated from the base end of another liquid flow passage by a side wall of the front end gasket accommodation part, each liquid flow passage being a groove concavely provided in the side wall of the front end gasket accommodation part and extending in an axial direction, and each liquid flow passage having a wide part having a gradually widening width in a base end of the side wall, through which a liquid medicine can pass when the front end gasket is accommodated in the front end gasket accommodation part, a sectional area of a front end of each liquid flow passage being smaller than a sectional area of a base end of the liquid flow passage.

2. The pre-filled syringe according to claim 1, further comprising an intermediate gasket located between the front end gasket in the barrel and the base end gasket and fluid-tightly partitioning an inside of the barrel into a front chamber and a rear chamber, and a bypass portion of the barrel bulging radially outward and located between the intermediate gasket of the barrel and the front end gasket.

3. A pre-filled syringe according to claim 2, characterized in that a sectional area of each liquid flow passage becomes gradually smaller from the base end of the liquid passage toward the front end of the liquid passage.

4. A pre-filled syringe according to claim 3, wherein in an outer periphery edge of a rear end face of the front end gasket, at least one concave part extending radially inward is provided.

5. A pre-filled syringe according to claim 4, wherein the intermediate gasket includes an annular seal part which contacts an inner wall of the barrel and fluid-tightly partitions the barrel into the front chamber and the rear chamber, and a bypass communication passage comprising a spiral groove formed in an outer wall of the intermediate gasket, which communicates the front chamber to the rear chamber through the bypass portion.

6. A pre-filled syringe according to claim 3, wherein the intermediate gasket includes an annular seal part which contacts an inner wall of the barrel and fluid-tightly partitions the barrel into the front chamber and the rear chamber, and a bypass communication passage comprising a spiral groove formed in an outer wall of the intermediate gasket, which communicates the front chamber to the rear chamber through the bypass portion.

7. A pre-filled syringe according to claim 2, wherein in an outer periphery edge of a rear end face of the front end gasket, at least one concave part extending radially inward is provided.

8. A pre-filled syringe according to claim 7, wherein the intermediate gasket includes an annular seal part which contacts an inner wall of the barrel and fluid-tightly partitions the barrel into the front chamber and the rear chamber, and a bypass communication passage comprising a spiral groove formed in an outer wall of the intermediate gasket, which communicates the front chamber to the rear chamber through the bypass portion.

9. A pre-filled syringe according to claim 2, wherein the intermediate gasket includes an annular seal part which contacts an inner wall of the barrel and fluid-tightly partitions the barrel into the front chamber and the rear chamber, and a bypass communication passage comprising a spiral groove formed in an outer wall of the intermediate gasket, which communicates the front chamber to the rear chamber through the bypass portion.

10. A pre-filled syringe according to claim 1, characterized in that a sectional area of each liquid flow passage becomes gradually smaller from the base end of the liquid passage toward the front end of the liquid passage.

11. A pre-filled syringe according to claim 10, wherein in an outer periphery edge of a rear end face of the front end gasket, at least one concave part extending radially inward is provided.

12. A pre-filled syringe according to claim 1, wherein in an outer periphery edge of a rear end face of the front end gasket, at least one concave part extending radially inward is provided.

* * * * *